(12) United States Patent
Glukhovsky et al.

(10) Patent No.: US 8,494,650 B2
(45) Date of Patent: Jul. 23, 2013

(54) INSERTION TOOLS AND METHODS FOR AN ELECTRICAL STIMULATION IMPLANT

(75) Inventors: Arkady Glukhovsky, Santa Clarita, CA (US); Yitzhak Zilberman, Santa Clarita, CA (US)

(73) Assignee: Bioness, Inc., Valencia, CA (US)

( * ) Notice: Subject to any disclaimer, the term of this patent is extended or adjusted under 35 U.S.C. 154(b) by 605 days.

(21) Appl. No.: 12/187,662

(22) Filed: Aug. 7, 2008

(65) Prior Publication Data

US 2010/0036465 A1 Feb. 11, 2010

(51) Int. Cl.
*A61N 1/05* (2006.01)
(52) U.S. Cl.
USPC .......................................................... 607/116
(58) Field of Classification Search
USPC .......................................................... 607/116
See application file for complete search history.

(56) References Cited

U.S. PATENT DOCUMENTS

| | | | |
|---|---|---|---|
| 2,438,786 A * | 3/1948 | Moore | 401/135 |
| 4,166,469 A | 9/1979 | Littleford | |
| 4,596,553 A | 6/1986 | Lee | |
| 5,003,990 A | 4/1991 | Osypka | |
| 5,292,309 A | 3/1994 | Van Tassel et al. | |
| 5,304,218 A | 4/1994 | Alferness | |
| 5,443,493 A | 8/1995 | Byers et al. | |
| 5,586,553 A | 12/1996 | Halili et al. | |
| 5,667,514 A | 9/1997 | Heller | |
| 5,782,841 A | 7/1998 | Ritz et al. | |
| 5,797,923 A | 8/1998 | Aiyar et al. | |
| 5,984,890 A | 11/1999 | Gast et al. | |
| 6,051,017 A | 4/2000 | Loeb et al. | |
| 6,132,456 A | 10/2000 | Sommer et al. | |
| 6,149,657 A | 11/2000 | Kuzma | |
| 6,185,464 B1 | 2/2001 | Bonner et al. | |
| 6,304,785 B1 | 10/2001 | McCreery et al. | |
| 6,332,089 B1 | 12/2001 | Acker et al. | |
| 6,337,994 B1 | 1/2002 | Stoianovici et al. | |
| 6,360,750 B1 | 3/2002 | Gerber et al. | |
| 6,379,346 B1 | 4/2002 | McIvor et al. | |
| 6,582,441 B1 | 6/2003 | He et al. | |
| 6,697,677 B2 | 2/2004 | Dahl et al. | |
| 6,829,508 B2 | 12/2004 | Schulman et al. | |
| 6,968,238 B1 | 11/2005 | Kuzma | |

(Continued)

FOREIGN PATENT DOCUMENTS

WO WO 2009/088563 7/2009

OTHER PUBLICATIONS

Search Report for International Application No. PCT/US2009/050648, mailed Oct. 22, 2009, 3 pages.

(Continued)

*Primary Examiner* — Christopher D Koharski
*Assistant Examiner* — Michael D Abreu
(74) *Attorney, Agent, or Firm* — Cooley LLP

(57) ABSTRACT

In some embodiments, a method includes inserting at least a distal end portion of an insertion tool within a body. The distal end portion of the insertion tool is coupled to an electronic implant having a stimulation portion, a terminal portion and a substantially flexible conductor disposed between the stimulation portion and the terminal portion. The distal end portion of the insertion tool is moved within the body such that the stimulation portion of the electronic implant is disposed adjacent a target location and the terminal portion of the electronic implant is disposed beneath a skin of the body.

12 Claims, 7 Drawing Sheets

U.S. PATENT DOCUMENTS

| | | |
|---|---|---|
| 6,999,819 B2 | 2/2006 | Swoyer et al. |
| 7,018,384 B2 | 3/2006 | Skakoon |
| 7,050,858 B1 | 5/2006 | Kuzma et al. |
| 7,063,708 B2 | 6/2006 | Gibson et al. |
| 7,151,965 B2 | 12/2006 | Osypka |
| 7,155,287 B2 | 12/2006 | Gavronsky |
| 7,200,444 B2 | 4/2007 | Gavronsky et al. |
| 7,513,257 B2 | 4/2009 | Schulman et al. |
| 7,526,342 B2 | 4/2009 | Chin et al. |
| 7,603,159 B2 | 10/2009 | Rasche |
| 7,621,754 B2 | 11/2009 | Costello |
| 7,655,014 B2 | 2/2010 | Ko et al. |
| 7,684,858 B2 | 3/2010 | He et al. |
| 2002/0042594 A1 | 4/2002 | Lum et al. |
| 2003/0028232 A1 | 2/2003 | Camps et al. |
| 2003/0078618 A1 | 4/2003 | Fey et al. |
| 2003/0143895 A1 | 7/2003 | Sommer et al. |
| 2004/0034351 A1 | 2/2004 | Sherman et al. |
| 2004/0116878 A1 | 6/2004 | Byrd et al. |
| 2005/0113894 A1 | 5/2005 | Zilberman et al. |
| 2005/0119660 A1 | 6/2005 | Bourlion et al. |
| 2005/0251237 A1 | 11/2005 | Kuzma et al. |
| 2006/0111728 A1 | 5/2006 | Abdou |
| 2006/0217705 A1 | 9/2006 | Godara et al. |
| 2006/0293626 A1 | 12/2006 | Byrum et al. |
| 2007/0038052 A1 | 2/2007 | Swoyer et al. |
| 2007/0078503 A1 | 4/2007 | Kuzma et al. |
| 2007/0156012 A1 | 7/2007 | Tracey et al. |
| 2007/0249992 A1 | 10/2007 | Bardy |
| 2008/0033356 A1 | 2/2008 | Kluge et al. |
| 2008/0269740 A1 | 10/2008 | Bonde et al. |
| 2009/0105743 A1 | 4/2009 | Chu |
| 2009/0182401 A1 | 7/2009 | Glukhovsky |
| 2009/0182402 A1 | 7/2009 | Glukhovsky |
| 2009/0182403 A1 | 7/2009 | Glukhovsky |
| 2010/0174306 A1 | 7/2010 | Mitelberg et al. |
| 2010/0240240 A1 | 9/2010 | Ochoa et al. |

OTHER PUBLICATIONS

Non-Final Office Action for U.S. Appl. No. 12/407,097, mailed Jan. 20, 2011.
Non-Final Office Action for U.S. Appl. No. 11/856,833, mailed Jan. 19, 2011.
Office Action for U.S. Appl. No. 11/856,833, mailed Jun. 13, 2011.
Supplementary European Search Report for European Application No. 09805333.3, mailed Dec. 21, 2012.

* cited by examiner

INSERTION TOOLS AND METHODS FOR AN ELECTRICAL STIMULATION IMPLANT

BACKGROUND

The invention relates generally to medical devices and procedures, and more particularly to insertion tools and methods for implanting electrical stimulation implants within the body.

Known electrical stimulation implants are used in various medical procedures. For example, some known electrical stimulation implants can be implanted within a patient's body to stimulate a response from a bodily organ or tissue, such as, for example, the heart, a muscle group or the like. Some known electrical stimulation implants can include a stimulation end, such as a cuff electrode, a pick-up end and a conductive portion therebetween. Such known electrical stimulation implants can be inserted into the patient's body in a predetermined location and/or orientation (e.g., such that the stimulation end is located adjacent a target location and the pick-up end is located beneath the skin).

Known methods for implanting an electrical stimulation implant within a patient's body can include first inserting the stimulation end of the implant adjacent the target tissue, and then separately inserting the pick-up end of the implant under the surface of the skin. Such known methods, however, often include using multiple tools, such as, for example, a tool to insert the stimulation end of the implant and a different tool to insert the pick-up end of the implant. Moreover, such known methods also include inserting the pick-up end of the implant into the body via a pathway different from the pathway through which the stimulation end of the implant is inserted into the body.

Known methods for stimulating a desired target tissue via an electrical stimulation implant within a patient's body can include first placing a pair of surface electrodes on the patient's skin. A current can then be conveyed transcutaneously from the surface electrode to the target tissue via the implant. Such known methods, however, can often result in weak stimulation due to attenuation of the current as the current travels within the body.

Thus, a need exists for improved methods and apparatus for implanting an electrical stimulation implant within a patient's body. Additionally, a need exists for improved methods of delivering current to an electrical stimulation implant within a patient's body.

SUMMARY

Methods and apparatus for inserting an electrical stimulation implant are described herein. In some embodiments, a method includes inserting at least a distal end portion of an insertion tool into a body. The distal end portion of the insertion tool is coupled to an electronic implant having a stimulation portion, a terminal portion and a substantially flexible conductor disposed between the stimulation portion and the terminal portion. The distal end portion of the insertion tool is moved within the body such that the stimulation portion of the electronic implant is disposed adjacent a target location and the terminal portion of the electronic implant is disposed beneath a skin of the body.

DETAILED DESCRIPTION

Figure 1:
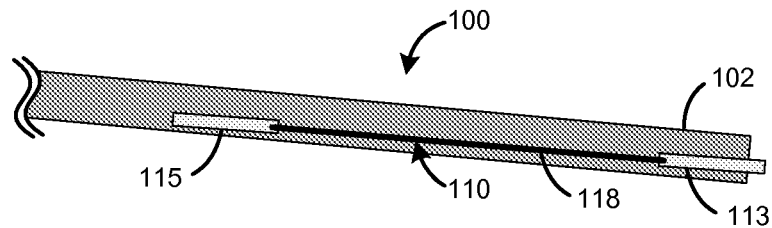
FIG. 1 is a schematic illustration of an insertion tool including an electronic implant according to an embodiment.

In some embodiments, a method includes inserting at least a distal end portion of an insertion tool into a body. The distal end portion of the insertion tool is coupled to an electronic implant having a stimulation portion, a terminal portion and a substantially flexible conductor disposed between the stimulation portion and the terminal portion. The distal end portion of the insertion tool is moved within the body such that the stimulation portion of the electronic implant is disposed adjacent a target location and the terminal portion of the electronic implant is disposed beneath a skin of the body.

In some embodiments, an apparatus includes an implant delivery tool configured to deliver at least a portion of an electronic implant within a body. The implant delivery tool includes a guide member and an insertion member. The guide member has a distal end portion configured to contact an outer surface of a skin of the body. Additionally, the distal end portion of the guide member is configured to move relative to the outer surface of the skin. The insertion member is configured to deliver the portion of the electronic implant into the body when the distal end portion of the guide member is moved relative to the outer surface of the skin.

In some embodiments, a method includes operatively coupling an electrical device disposed outside of a body to a first electrode and a second electrode. The first electrode is coupled to a first portion of a skin of the body and the second electrode is coupled to a second portion of the skin. An electrical signal from the electrical device is conveyed into the body via the first electrode such that a first portion of the electrical signal travels within the body along a first path and a second portion of the electrical signal travels within the body along a second path. The first path, which can be, for example, a first stimulation path, includes the first portion of the skin, the second portion of the skin and a target location within the body. The target location can be, for example, a median nerve, a peripheral nerve, a superficially located nerve or the like. The second path, which can be, for example, a second stimulation path, includes the first portion of the skin, the second portion of the skin and an electronic implant disposed within the body.

As used in this specification, the words "proximal" and "distal" refer to the direction closer to and away from, respectively, an operator (e.g., surgeon, physician, nurse, technician, etc.) who would use a medical device during a procedure. For example, the end of a medical device first to contact and/or be inserted into the patient's body would be the distal end, while the opposite end of the medical device (e.g., the end of the medical device being operated by the operator) would be the proximal end of the medical device.

The term "electronic implant" as used herein can refer to either an implant including active electronic circuitry or an implant including a passive portion of an electronic circuit system, unless otherwise specified. For example, as used herein, an electronic implant can include active devices, such as microstimulators, amplifiers, power supplies, sensors or the like. An electronic implant can also include passive devices, such as passive conductors, leads, wires, or the like.

FIG. 1 is a schematic illustration of an insertion tool 100 and an electronic implant 110 according to an embodiment of the invention. The insertion tool 100 includes a distal end portion 102 and a proximal end portion (not shown). The electronic implant 110 is coupled to the distal end portion 102 of the insertion tool 100 and includes a stimulation portion 113, a terminal portion 115 and a conductor 118. The conductor 118, which is constructed of a substantially flexible material, is disposed between the stimulation portion 113 and the terminal portion 115 of the electronic implant 110. The insertion tool 100 is configured to insert an electronic implant 110 within a body of a patient. In some embodiments, the stimulation portion 113 of the electronic implant 110 stimulates a target location within the body. In some embodiments, the target location can be a median nerve, a peripheral nerve, a superficially located nerve or the like.

In some embodiments, the insertion tool 100 defines a lumen (not shown) within which the electronic implant 110 can be disposed. In other embodiments, the electronic implant 110 can be coupled to an outer surface of the distal end portion 102 of the insertion tool 100. Although FIG. 1 shows the electronic implant 110 being coupled to the distal end portion 102 of the insertion tool 100 such that the stimulation portion 113 of the electronic implant 110 extends beyond the distal end portion 102 of the insertion tool 100, in some embodiments, the electronic implant 110 can be coupled to the insertion tool 100 such that the stimulation portion 113 is flush with or recessed from the distal end portion 102 of the insertion tool 100.

The distal end portion 102 of the insertion tool 100 and the electronic implant 110 can be coupled together by any suitable means. For example, the distal end portion 102 of the insertion tool 100 and the electronic implant 110 can be coupled together by a mechanical coupling (e.g., an interference fit, detents, a threaded coupling, or the like), an electronic coupling (e.g., a magnetic coupling), a chemical bond, a hydraulic coupling and/or a pneumatic coupling (e.g., a vacuum coupling). Although the electronic implant 110 is shown as being coupled to the distal-most portion of the insertion tool 100, in other embodiments, the electronic implant 110 can be coupled in any suitable location along the distal end portion 102 of the insertion tool 100.

The insertion tool 100 can be any suitable shape and/or size to facilitate percutaneous insertion of the insertion tool 100 within the body. For example, the insertion tool 100 can have a cylindrical shape and a diameter of approximately 1 millimeter. In some embodiments, the distal end portion 102 of the insertion tool 100 can have a tapered portion. In some embodiments, however, the insertion tool 100 can be used during an open surgery and can be any suitable size and/or shape to facilitate such insertion.

Figure 2:
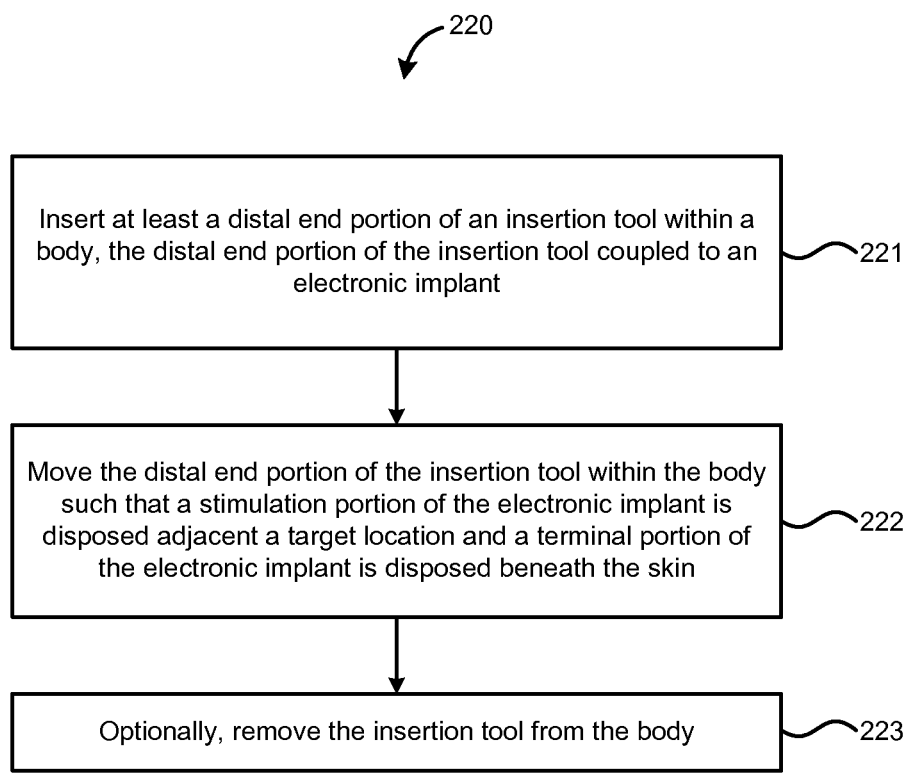
FIG. 2 is a flow chart of a method of inserting the electronic implant into the body using the insertion tool in FIG. 1.
Figure 3:
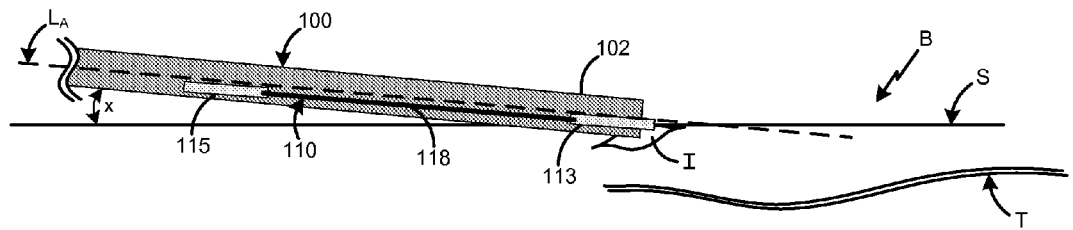
FIGS. 3-5 are schematic illustrations showing a method of inserting the electronic implant into the body using the insertion tool in FIG. 1.

FIG. 2 is a flow chart of a method 220 of disposing the electronic implant 110 within the body B according to an embodiment of the invention. The method illustrated in FIG. 2 is discussed with reference to FIGS. 3-5, which are schematic illustrations of the electronic implant 110 disposed within a body B in a first configuration, a second configuration and a third configuration, respectively. The method includes inserting at least a distal end portion of an insertion tool having an electronic implant coupled thereto into a body, 221. Referring to FIG. 3, at least the distal end portion 102 of the insertion tool 100 is inserted into a body B of a patient through skin incision I. In some embodiments, the electronic implant 110 is coupled to the distal end portion 102 of the insertion tool 100 such that the stimulation portion 113 of the electronic implant 110 is inserted into the body B along with the distal end portion 102 of the insertion tool 100.

As shown in FIG. 3, the insertion tool 100 is inserted within the body B along the longitudinal axis $L_A$ of the insertion tool 100 at an angle x such that the insertion tool 100 is directed toward a target location T within the body B. In some embodiments, for example, the target location T can be a median nerve, a peripheral nerve, a superficially located nerve or the like. In some embodiments, the method can include inserting the insertion tool 100 such that the angle x of insertion is less than 30 degrees. Said another way, in some embodiments, the longitudinal axis $L_A$ of the insertion tool 100 can be offset from the skin S of the body B at an angle less than 30 degrees. In this manner, the insertion tool 100 can deliver the electronic implant 110 to a shallow target location within the body B.

Figure 4:
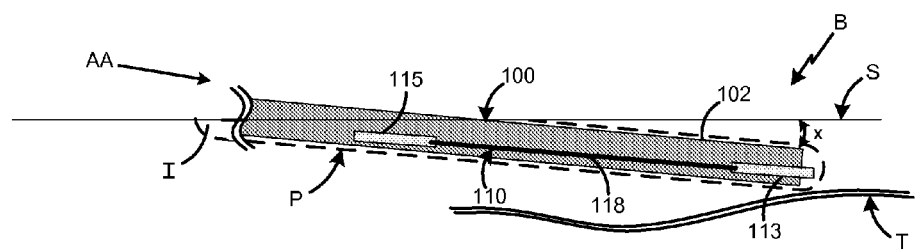

Returning to the flow chart shown in FIG. 2, the distal end portion of the insertion tool is moved within the body such that the stimulation portion of the electronic implant is disposed adjacent the target location and a terminal portion of the electronic implant is disposed beneath the skin, 222. As shown in FIG. 4, the insertion tool 100 is moved within the body B along the longitudinal axis $L_A$ of the insertion tool 100 in a direction AA, toward the target location T. The distal end portion 102 of the insertion tool 100 is moved along an insertion path P within the body B, such that the stimulation portion 113 of the electronic implant 110 is adjacent the target location T. Said another way, the distal end portion 102 of the insertion tool 100 is moved such that the stimulation portion 113 of the electronic implant 110 is spaced apart from the target location T within the patient's body B by a predetermined distance. Similarly stated, the stimulation portion 113 of the electronic implant 110 is positioned proximate a particular anatomical structure (e.g., a nerve, muscle, or the like), at a desired depth or the like. Although the stimulation portion 113 is shown as being adjacent the target location T, in other embodiments, the insertion tool 100 can be moved along the insertion path P such that the stimulation portion 113 of the electronic implant 110 is in contact with the target location T.

As shown in FIG. 4, the distal end portion 102 of the insertion tool 100 is moved along the insertion path P within the body B such that the terminal portion 115 of the electronic implant 110 is disposed beneath the skin S of the body B. In this manner, the stimulation portion 113 and the terminal portion 115 are implanted within the body B using the insertion tool 100, in a single motion. In some embodiments, the stimulation portion 113 and the terminal portion 115 of the electronic implant 110 are each disposed within the insertion path P. In some embodiments, the insertion tool 100 is moved within the body B such that the distal end portion 102 of the insertion tool 100 and/or the stimulation portion 113 of the insertion tool 100 defines the insertion path P. In some embodiments, for example, the distal end portion 102 of the insertion tool 100 can be configured to pierce, dilate and/or displace bodily tissue to define the insertion path P. In other embodiments, the insertion path P can be formed by a separate tool, such as, for example, an insertion probe, a trocar or the like.

Figure 5:
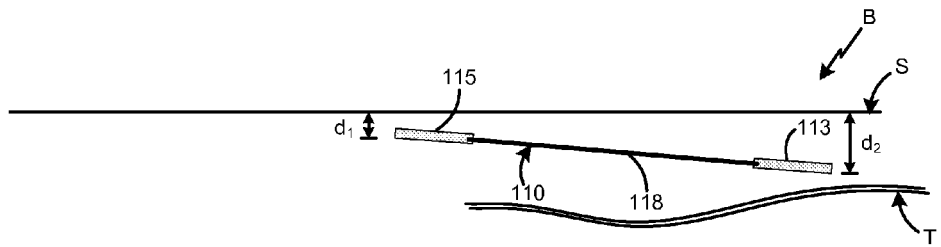

Returning to the flow chart shown in FIG. 2, in some embodiments, the insertion tool can be removed from the body, 223. As shown in FIG. 5, the insertion tool 100 is removed from the body B such that the electronic implant 110 remains in the body B at a predetermined location. Said another way, the electronic implant 110 substantially maintains a position within the body B after the insertion tool 100 is removed. In this manner, the stimulation portion 113 of the electronic implant 110 is adjacent the target location T at a predetermined depth, $d_2$, beneath the skin S of the body B. Similarly, the terminal portion 115 of the electronic implant 110 is beneath the skin S of the body B at a predetermined depth, $d_1$.

Figure 6:
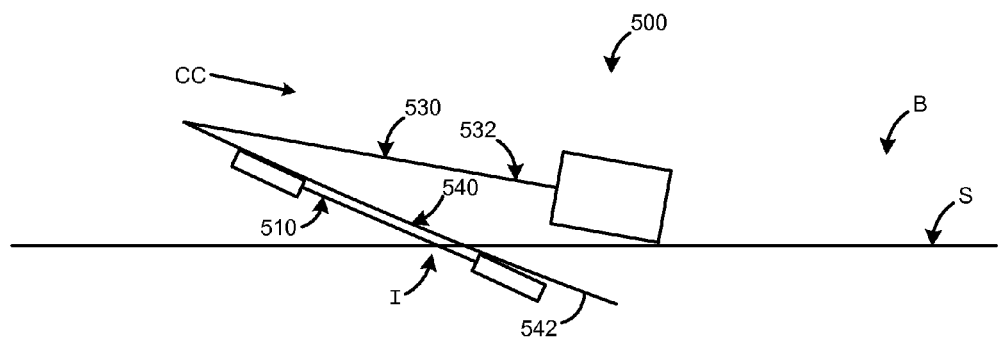
FIGS. 6 and 7 are schematic illustrations of an implant delivery tool according to an embodiment in a first configuration and a second configuration, respectively.
Figure 7:
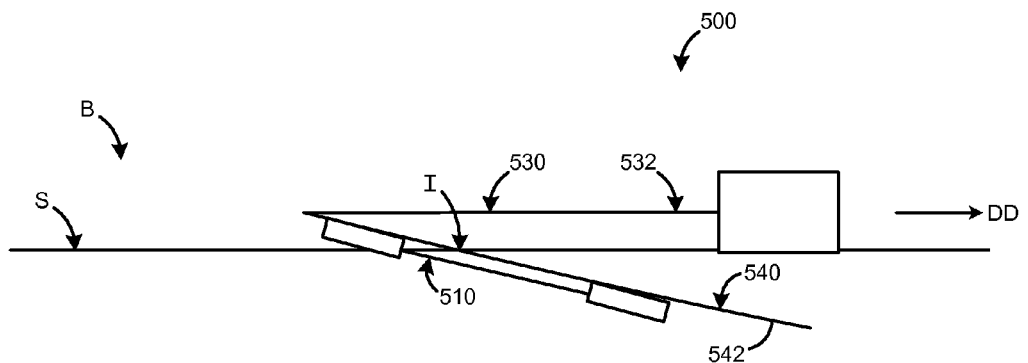

FIGS. 6 and 7 are schematic illustrations of an implant delivery tool 500 in a first configuration and a second configuration, respectively. The implant delivery tool 500 includes a guide member 530 and an insertion member 540. The guide member 530 of the implant delivery tool 500 includes a distal end portion 532 configured to contact an outer surface of a skin S of a body B and to move relative to the outer surface of the skin S.

The distal end portion 532 of the guide member 530 can have any size and/or shape to facilitate movement of the guide member 530 along the outer surface of the skin S. Said another way, the guide member 530 can have any size and/or shape that prevents the distal end portion 532 of the guide member 530 from catching and/or engaging the skin S such that the movement of the distal end portion 532 relative to the skin S is disrupted. In some embodiments, the distal end portion 532 of the guide member 530 can have a spherical shape to facilitate the movement of the guide member 530 along the outer surface of the skin S. In some embodiments, the distal end portion 532 of the guide member 530 can slide along the outer surface of the skin S. Similarly stated, the distal end portion 532 of the guide member 530 can translate along the outer surface of the skin S. In other embodiments, the distal end portion 532 of the guide member 530 can roll along the outer surface of the skin S. Similarly stated, the distal end portion 532 of the guide member 530 can rotate along the outer surface of the skin S.

The insertion member 540 of the implant delivery tool 500 includes a distal end portion 542 configured to be disposed within the body B. The insertion member 540 is configured to be coupled to an electronic implant 510. The electronic implant 510 can be, for example, a microstimulator, an elongate implant, an electronic lead, an electrode, a sensor and/or the like. In some embodiments, the insertion member 540 defines a lumen (not shown) within which at least a portion of the electronic implant 510 can be disposed. In some embodiments, at least a portion of the insertion member 540 can have an arcuate shape to facilitate the insertion of the electronic implant 510. In some embodiments, however, the insertion member 540 can be any size and/or shape to facilitate the delivery of the electronic implant 510 into the body B.

As shown in FIGS. 6 and 7, the guide member 530 is coupled to the insertion member 540 such that the movement of the guide member 530 results in the movement of the insertion member 540. In this manner, the guide member 530 is configured to guide the insertion member 540 within the body B during insertion of the insertion member 540. Similarly stated, the guide member 530 is configured to maintain the insertion member 540 at a predetermined depth within the body B when the insertion member 540 is inserted into the body B. Thus, a portion of an electronic implant 510 can be delivered into the body B via the insertion member 540 when the distal end portion 532 of the guide member 530 is moved relative to the outer surface of the skin S.

In the first configuration, as shown in FIG. 6, the implant delivery tool 500 is moved in direction CC such that the guide member 530 moves along the outer surface of the skin S and guides distal end portion 542 of the insertion member 540 as it is inserted into the body B via skin incision I. The shape of the insertion member 540 can define the path along which the insertion member 540 moves within the body B. In some embodiments, the insertion member 540 moves within the body B along a path formed by a separate tool, such as, for example, an insertion probe, a trocar or the like. As more of the insertion member 540 is inserted into the body, the implant delivery tool moves from the first configuration to the second configuration, as shown in FIG. 7. Similarly stated, when moved from the first configuration to the second configuration, the insertion tool 500 is moved in direction DD substantially parallel to the outer surface of the skin S. The insertion tool 500 is moved in direction DD until the electronic implant 510 is at its predetermined target location.

Figure 8:
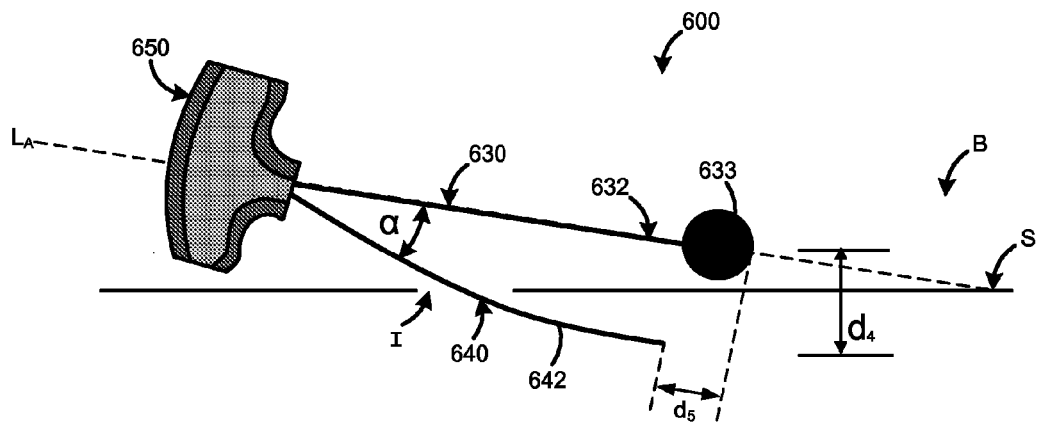
FIG. 8 is a perspective view of an implant delivery tool according to an embodiment.

FIG. 8 is a schematic illustration of an implant delivery tool 600 according to an embodiment of the invention. The implant delivery tool 600 includes a guide member 630, an insertion member 640 and a handle 650. The insertion member 640 and the guide member 630 are coupled together via the handle 650. The handle 650 is shaped such that a user can grasp the handle 650 to maneuver the implant delivery tool 600. The handle 650 can be any shape and/or size to facilitate the maneuvering of the implant delivery tool 600, such as, for example, a bulb shape.

The guide member 630 of the implant delivery tool 600 includes a distal end portion 632 configured to contact an outer surface of a skin S of a body B and to move relative to the outer surface of the skin S along a longitudinal axis $L_A$. The distal end portion 632 of the guide member 630 includes a spherical portion 633 to facilitate a movement of the guide member 630 along the outer surface of the skin S along the longitudinal axis $L_A$. Specifically, the distal end portion 632 of the guide member 630 slides along the outer surface of the skin S along the longitudinal axis $L_A$. Similarly stated, the distal end portion 632 of the guide member 630 translates along the longitudinal axis $L_A$. In this manner, the spherical portion 633 of the guide member 630 prevents the distal end portion 632 from catching and/or engaging the skin S such that the movement of the distal end portion 632 relative to the skin S is disrupted. In some embodiments, the spherical portion 633 of the guide member 630 can roll along the outer surface of the skin S. Similarly stated, the spherical portion 633 of the guide member 630 can rotate along the outer surface of the skin S.

The insertion member 640 includes a distal end portion 642 configured to be disposed within the body B, as shown in FIG. 8. The insertion member 640 is configured to be coupled to an electronic implant (not shown). The electronic implant can be, for example, a microstimulator, an elongate implant, an electronic lead, an electrode, a sensors and/or the like. The insertion member 640 has an arcuate shape to facilitate the insertion of the electronic implant (not shown). In some embodiments, however, the insertion member 640 can be any size or shape to facilitate the delivery of the electronic implant into the body B. In some embodiments, the insertion member 640 is configured to be coupled to the electronic implant such that a portion of the electronic implant can be delivered into the body B via skin incision I when the distal end portion 632 of the guide member 630 is moved relative to the outer surface of the skin S.

The guide member 630 and the insertion member 640 are positioned relative to each other at an angle α. Said another way, the insertion member 640 is oriented at angle α relative to the longitudinal axis $L_A$ of the guide member 630. In this manner, the distal end portion 632 of the guide member 630 is separated from the distal end portion 642 of the insertion member 640 by a distance $d_4$. In some embodiments, a user, such as, for example, a surgeon, can determine the angle α of orientation of the guide member 630 relative to the insertion member 640 and/or the distance $d_4$ between the guide member 630 and the insertion member 640.

As shown in FIG. 8, the distal end portion 642 of the insertion member 640 is displaced from the end of the spherical portion 633 of the guide member 630 along the longitudinal axis $L_A$ of the guide member 630 by a distance $d_5$. In other embodiments, however, the distal end portion 642 of the insertion member 640 can be flush with the spherical portion 633 of the guide member 630. In yet other embodiments, the distal end portion 642 of the insertion member 640 can extend beyond the spherical portion 633 of the guide member 630.

In some embodiments, the spherical portion 633 can include an electronic device configured to convey information back to a user. Such information can be, for example, information relating to the location of the insertion member 640 within the body B. In other embodiments, the spherical portion 633 of the guide member 630 can be configured to electrically stimulate a target location within the body B.

In some embodiments, the distal end portion 642 of the insertion member 640 is configured to locate a target location within the body B. For example, in some embodiments, the distal end portion 642 of the insertion member 640 can include a target probe having an exposed electrode configured to stimulate a muscle, a nerve or the like and/or receive an electronic signal from a muscle, nerve or the like to locate the target location.

In some embodiments, the handle 650 can be configured to adjust the angle α of orientation between the guide member 630 and the insertion member 640. Similarly, the handle 650 can be configured to adjust the distance $d_4$ between the distal end portion 632 of the guide member 630 and the distal end portion 642 of the insertion member 640.

In some embodiments, the insertion member 640 can include a plurality of graduated markings configured to indicate a position of the distal end portion 642 of the insertion member 640 within the body B. In some embodiments, the insertion member 640 can be configured to have an adjustable length.

In some embodiments, the insertion member 640 and/or the guide member 630 of the implant delivery tool 600 can be similar to portions of the insertion tool shown in U.S. patent application Ser. Nos. 11/972,393, 11/972,396, and 11/972,402 to Glukhovsky, which are incorporated by reference for all purposes as if fully set forth herein.

Figure 9:
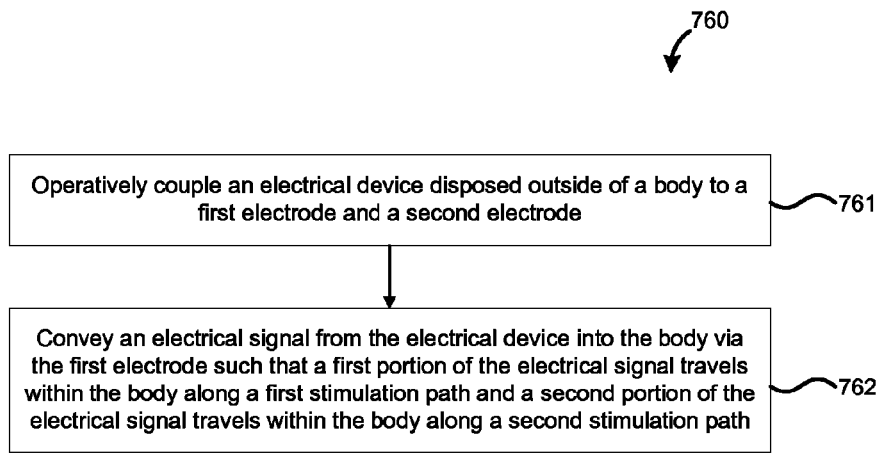
FIG. 9 is a flow chart of a method of stimulating a target location within a body according to an embodiment.
Figure 10:
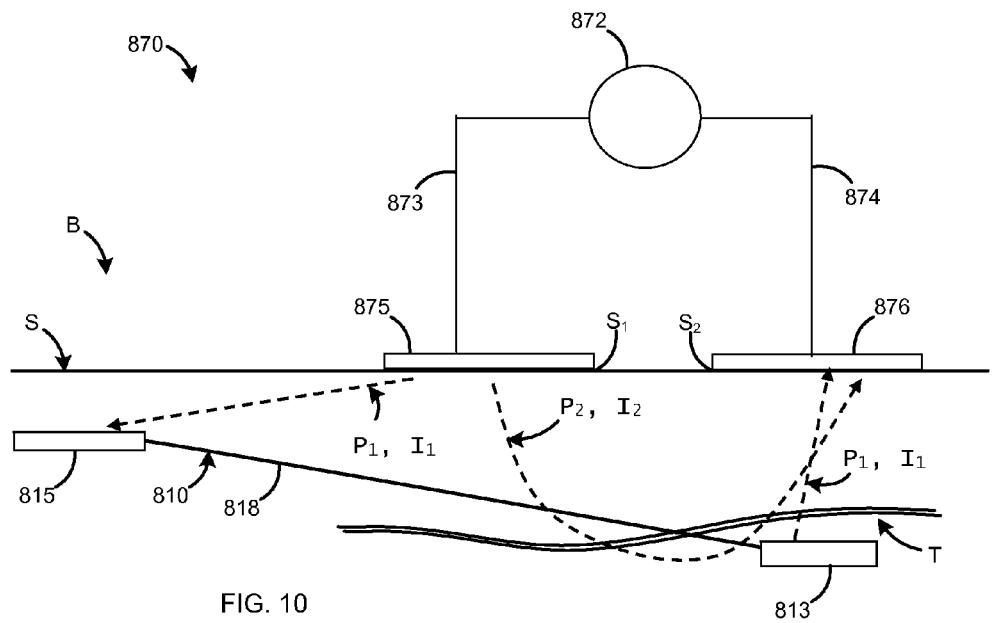
FIG. 10 is a schematic illustration of an electrical stimulation system according to an embodiment.

FIG. 9 is a flow chart of a method 760 of stimulating a target location T within a body B according to an embodiment of the invention. The method illustrated in FIG. 9 is discussed with reference to FIG. 10, which is a schematic illustration of an electrical stimulation system 870 for stimulating a target location T within a body B. The method includes operatively coupling an electrical device disposed outside of a body to a first electrode and a second electrode, 761. Referring to FIG. 10, the electrical stimulation system 870 includes an electrical device 872, a first electrode 875 and a second electrode 876. The electrical device 872 is operatively coupled to the first electrode 875 via a first connection 873. Similarly, the electrical device 872 is operatively coupled to the second electrode 876 via a second connection 874. The electrical device 872 is configured to generate and send an electrical signal to the first electrode 875 and/or the second electrode 876 via connections 873 and 874, respectively. In some embodiments, for example, the electrical device 872 can produce an electrical current having characteristics suitable for therapeutic stimulation. In some embodiments, the connections 873 and 874 are wires. In some embodiments, the connections 873 and 874 are direct electrical contacts between the electrical device 872 and the electrodes 875 and 876.

The first electrode 875 and the second electrode 876 are surface electrodes disposed on an outer surface of a skin S of the body B. More specifically, the first electrode 875 is coupled to a first portion $S_1$ of the skin S and the second electrode 876 is coupled to a second portion $S_2$ of the skin S. In some embodiments, the first electrode 875 and the second electrode 876 are spaced apart from each other by a predetermined distance. Said another way, in some embodiments, the first portion $S_1$ of the skin S is disposed apart from the second portion $S_2$ of the skin S. The location of the electrodes 875 and 876 can be maintained by any suitable means, such as, for example, a conductive gel, adhesive, a fitted garment or the like. The electrodes 875 and 876 can be any suitable electrode for transmitting and/or receiving an electrical signal to or from the body B. For example, in some embodiments, the electrodes 875 and 876 can be gel electrodes. In other embodiments, the electrodes 875 and 876 can be flexible disc-type electrodes having electrical leads. Similarly, the electrodes 875 and 876 can be constructed from any suitable material, such as, for example, conductive electrolyte gel, conductive rubber, conductive plastic, metal mesh, metal plate, metallized rubber and/or plastic.

As shown in FIG. 10, an electronic implant 810 is disposed beneath the skin S of the body B. The electronic implant 810 includes a stimulation portion 813, a terminal portion 815 and a conductor 818. The conductor 818 is disposed between the stimulation portion 813 and the terminal portion 815 of the electronic implant 810. The stimulation portion 813 of the electronic implant 810 is disposed adjacent a target location T and is configured to electrically stimulate the target location T. As shown in FIG. 10, the second electrode 876 is coupled to the skin S in a location above the stimulation portion 813 of the electronic implant 810. In some embodiments, the second electrode 876 can be coupled to the skin at a location directly above the stimulation portion 813 of the electronic implant 810 and/or the target location T. The first electrode 875 is coupled to the skin S in a location adjacent the terminal portion 815 of the electronic implant 810. In some embodiments, the first electrode 875 can be coupled to the skin S at a location directly above the terminal portion 815 of the electronic implant 810.

Returning to the flow chart shown in FIG. 9, an electrical signal is conveyed from the electrical device into the body via the first electrode such that a first portion of the electrical signal travels within the body along a first path and a second portion of the electrical signal travels within the body along a second path, 762. Referring to FIG. 10, the electrical device 872 conveys an electrical signal (e.g., current) transcutaneously into the body B via the first electrode 875. When the electrical signal is conveyed into the body B, a first portion $I_1$ of the signal travels along a first path $P_1$ and a second portion $I_2$ of the signal travels along a second path $P_2$. The first path $P_1$, which can be, for example, a first stimulation path, includes the first electrode 875, the electronic implant 810 and the second electrode 876. In this manner, the first portion $I_1$ of the electrical signal travels along the first path $P_1$ from the first electrode 875 to the terminal portion 815 of the electronic implant 810, through the first portion $S_1$ of the skin S of the body B. The first portion $I_1$ of the electrical signal is received by the terminal portion 815 of the electronic implant 810 and is conveyed to the stimulation portion 813 of the electronic implant 810 via the conductor 818. Thus, first portion $I_1$ of the electrical signal stimulates the target location T via the stimulation portion 813 of the electronic implant 810. The first portion $I_1$ of the electrical signal is transmitted back to the second electrode 876, through the second portion $S_2$ of the skin S of the body B, to complete the electrical circuit.

As shown in FIG. 10, the second path $P_2$, which can be, for example, a second stimulation path, includes the first electrode 875, the target location T and the second electrode 876. In this manner, the second portion $I_2$ of the electrical signal travels along the second path $P_2$ from the first electrode 875 to the target location T, through the first portion $S_1$ of the skin S of the body B, such that the target location T is stimulated via the second portion $I_2$ of the electrical signal. The second portion $I_2$ of the electrical signal is transmitted back to the second electrode 876, through the second portion $S_2$ of the skin S of the body B, to complete the electrical circuit.

Figure 11:
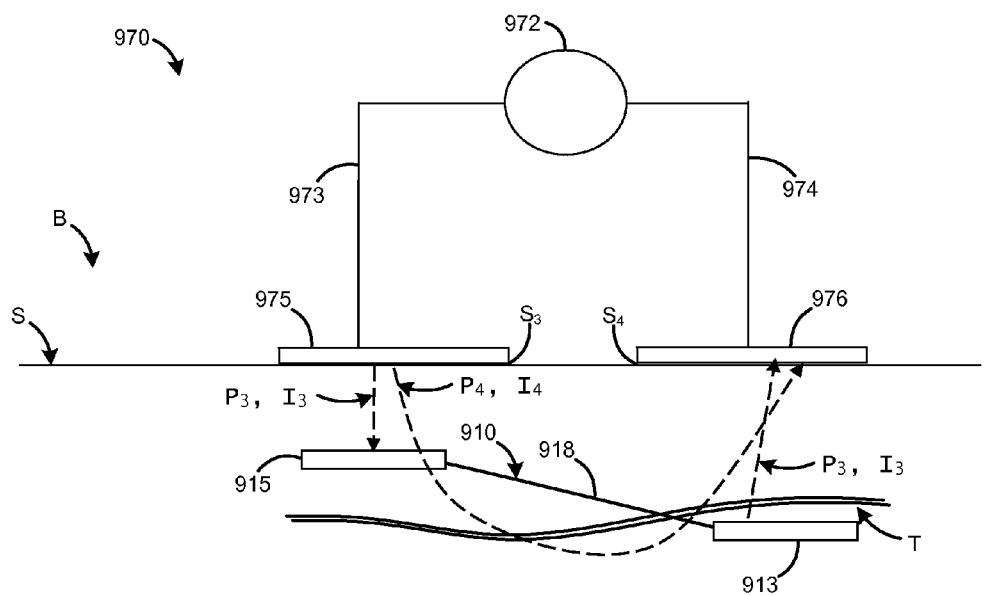
FIG. 11 is a schematic illustration of an electrical stimulation system according to an embodiment.

FIG. 11 is a schematic illustration of a electrical stimulation system 970 for stimulation of a target location T within a body B. The electrical stimulation system 970 includes an electrical device 972, a first electrode 975 and a second electrode 976. The electrical device 972 is operatively coupled to the first electrode 975 via a first connection 973. Similarly, the electrical device 972 is operatively coupled to the second electrode 976 via a second connection 974. The electrical device 972 is configured to generate and send an electrical signal to the first electrode 975 and/or the second electrode 976 via connections 973 and 974, respectively. In some embodiments, for example, the electrical device 972 can produce an electrical current having characteristics suitable for therapeutic stimulation. In some embodiments, the connections 973 and 974 are wires. In some embodiments, the connections 973 and 974 are direct electrical contacts between the electrical device 972 and the electrodes 975 and 976.

The first electrode 975 and the second electrode 976 are surface electrodes disposed on an outer surface of a skin S of the body B. More specifically, the first electrode 975 is coupled to a first portion $S_3$ of the skin S and the second electrode 976 is coupled to a second portion $S_4$ of the skin S, as described above with reference to FIG. 10. In some embodiments, the first electrode 975 and the second electrode 976 are spaced apart from each other by a predetermined distance. Said another way, in some embodiments, the first portion of the skin S is disposed apart from the second portion of the skin S. The location of the electrodes 975 and 976 can be maintained by any suitable means, as described above. The electrodes 975 and 976 can be any suitable electrode for transmitting and/or receiving an electrical signal to or from the body B, as described above.

As shown in FIG. 11, an electronic implant 910 is disposed beneath the skin S of the body B. The electronic implant 910 includes a stimulation portion 913, a terminal portion 915 and a conductor 918. The conductor 918 is disposed between the stimulation portion 913 and the terminal portion 915 of the electronic implant 910. The stimulation portion 913 of the electronic implant 910 is disposed adjacent a target location T and is configured to electrically stimulate the target location T. As shown in FIG. 15, the electronic implant 910 has length such that the terminal portion 915 of the electronic implant 910 is disposed below the first electrode 975 and the stimulation portion 913 of the electronic implant 910 is disposed below the second electrode 976. Said another way, the second electrode 976 is coupled to the skin S in a location above the stimulation portion 913 of the electronic implant 910. In some embodiments, the second electrode 976 can be coupled to the skin at a location directly above the stimulation portion 913 of the electronic implant 910 and/or the target location T. Similarly, the first electrode 975 is coupled to the skin S in a location above the terminal portion 915 of the electronic implant 910. In some embodiments, the first electrode 975 can be coupled to the skin S at a location directly above the terminal portion 915 of the electronic implant 910.

As shown in FIG. 11, the electrical device 972 conveys an electrical signal (e.g., current) transcutaneously into the body B via the first electrode 975. When the electrical signal is conveyed into the body B, a first portion $I_3$ of the signal travels along a first path $P_3$ and a second portion $I_4$ of the signal travels along a second path $P_4$. The first path $P_3$, which can be, for example, a first stimulation path, includes the first electrode 975, the electronic implant 910 and the first electrode 976. In this manner, the first portion $I_3$ of the signal travels along the first path $P_3$ from the first electrode 975 to the terminal portion 915 of the electronic implant 910, through the first portion $S_3$ of the skin S of the body B. The first portion 13 of the signal is received by the terminal portion 915 of the electronic implant 910 and is conveyed to the stimulation portion 913 of the electronic implant 910 via the conductor 918. Thus, the first portion $I_3$ of the signal stimulates the target location T via the stimulation portion 913 of the electronic implant 910. The first portion $I_3$ of the signal is transmitted back to the second electrode 976, through the second portion $S_4$ of the skin S of the body B, to complete the electrical circuit.

The second path $P_4$, which can be, for example, a second stimulation path, includes the first electrode 975, the target location T and the second electrode 976. In this manner, the second portion $I_4$ of the signal travels along the second path $P_4$ from the first electrode 975 to the target location T, through the first portion $S_3$ of the skin S of the body B, such that the target location T is stimulated via the second portion $I_4$ of the signal. The second portion $I_4$ of the signal is transmitted back to the second electrode 976, through the second portion $S_4$ of the skin S of the body B, to complete the electrical circuit.

As shown in FIGS. 10 and 11, the electrical stimulation system 870 and 970 can be placed on the skin S, above the electronic implant 810 and 910, in different configurations. The different configurations can be used to tailor stimulation to the target location T. Said another way, the configurations can be used to fine tune the stimulation such that attenuation of the electrical signal is minimized as the electrical signal is conveyed in the body B. Similarly stated, the configurations can be used to maximize the amount of the electrical signal that reaches the target location T. For example, in some embodiments, the electronic implant can have a short lead length such that the first electrode is positioned on the skin above the terminal portion of the electronic implant and the second electrode is positioned on the skin above the stimulation portion of the electronic implant. In this manner, the distance the first portion of the electrical signal has to travel to the terminal portion and the distance the second portion of the electrical signal has to travel to the target location T is minimized. Thus, a greater amount of the electrical signal reaches the target location T such that attenuation of the electrical signal is minimized. As a result, the electrical stimulation systems 870 and 970 are well-suited for shallow depth stimulation.

Figure 12:
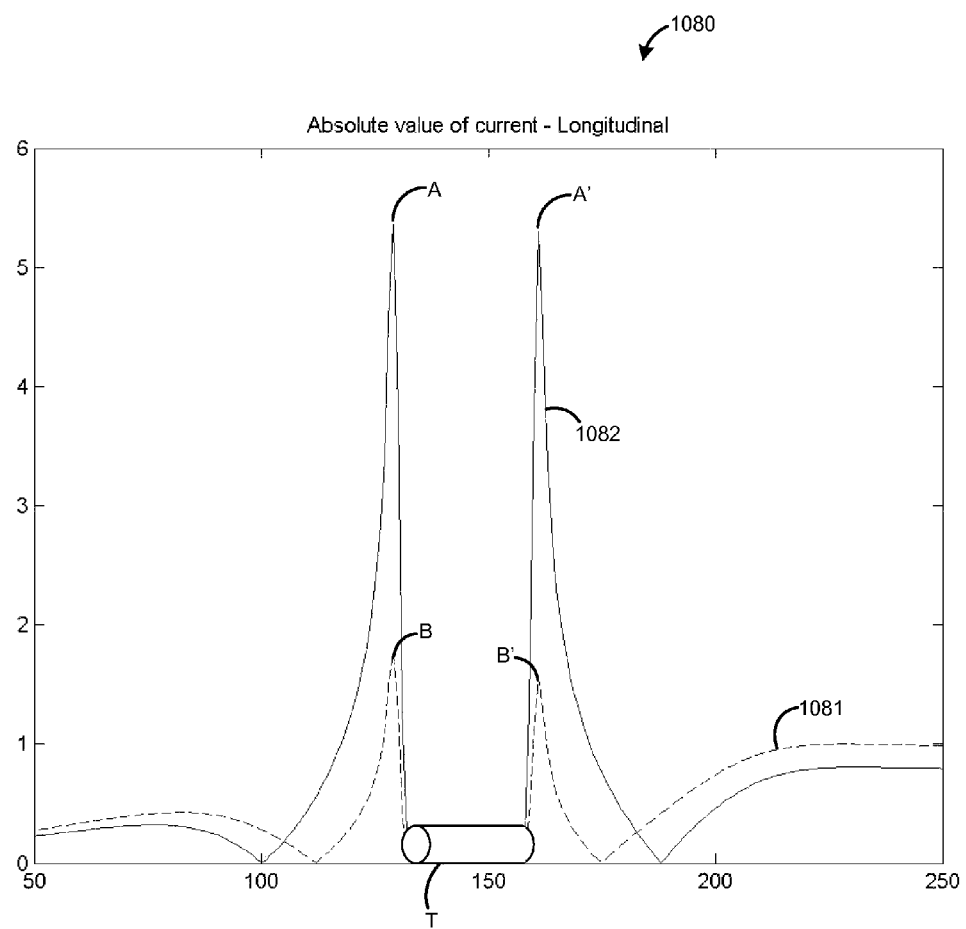
FIG. 12 is a plot of the absolute value of a simulated current distribution in a body of a patient along a longitudinal axis, according to an embodiment.
Figure 13:
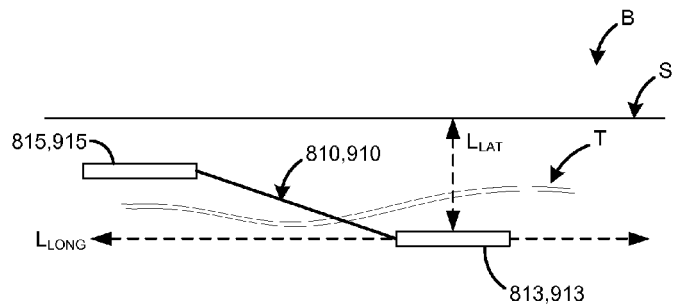
FIG. 13 is a schematic illustration of a longitudinal and a lateral axis across an electronic implant disposed within a body, according to an embodiment.

FIG. 12 is a plot 1080 of a simulated current distribution within the body B along a longitudinal axis $L_{LONG}$ of the stimulation portion 813 and 913 of the electronic implant 810 and 910. Specifically, the plot 1080 illustrates the simulated current distribution within the body B along an axis substantially parallel to the skin S of the body B, as shown in FIG. 13. Said another way, the plot 1080 illustrates the simulated current distribution within the body B along an axis substantially coaxial with the stimulation portion 813 and 913 of the electronic implant 810 and 910.

Referring to FIG. 12, a longitudinal current distribution 1081 of the electrical stimulation system 870 is represented by a dashed line and a longitudinal current distribution 1082 of the electrical stimulation system 970 is represented by a solid line. The current distributions 1081 and 1082 are representative of the net current distribution in the body B. More particularly, the current distribution 1081 is illustrative of the current distributed via the first portion $I_1$ and the second portion $I_2$ of the electrical signal. Similarly, the current distribution 1082 is illustrative of the current distributed via the first portion $I_3$ and the second portion $I_4$ of the electrical signal. Although the plot 1080 is shown as having numerical values on the x-axis and y-axis, such values are merely exemplary values. The x-axis of the plot 1080 is a spatial axis, which can be, for example, a distance from the target location T. The y-axis of the plot 1080 can have any relative value, such as, for example, current in Amperes.

As shown in FIG. 12, the highest amounts of current distribution within the body B are the areas nearest to the target location T. Specifically, the highest amounts of current distribution within the body B is located at points A and A' for electrical stimulation system 970 and at points B and B' for electrical stimulation system 870. The peak areas A, A', B and B' facilitate or help facilitate the stimulation of the target location T. More particularly, the higher current distributions within the body B nearest the target location T have a higher probability of activating the target location T. As described above, the amount of current distribution within the body B can be adjusted or tuned by the positioning of the electrodes of the electrical stimulation system.

Figure 14:
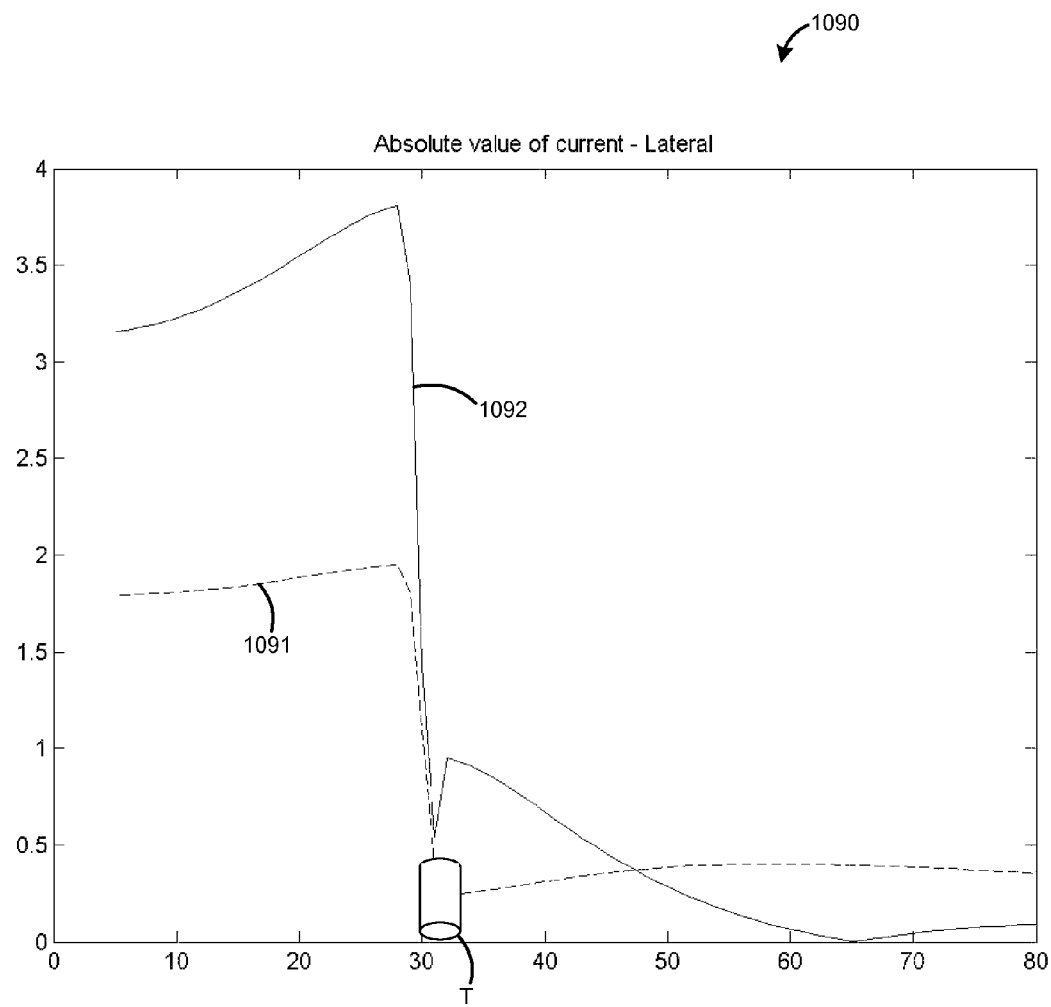
FIG. 14 is a plot of the absolute value of the simulated current distribution in a body of a patient along a lateral axis, according to an embodiment.

FIG. 14 is a plot 1090 of a simulated current distribution within the body B along a lateral axis $L_{LAT}$ of the stimulation portion 813 and 913 of the electronic implant 810 and 910. Specifically, the plot 1090 illustrates the simulated current distribution within the body B along an axis substantially perpendicular to the skin S of the body B, as shown in FIG. 13. Referring to FIG. 14, a lateral current distribution 1091 of the electrical stimulation system 870 is represented by a dashed line and a lateral current distribution 1092 of the electrical stimulation system 970 is represented by a solid line. The current distributions 1091 and 1092 are representative of the net current distribution in the body B, as described above with reference to plot 1080. Although the plot 1090 is shown as having numerical values on the x-axis and y-axis, such values are merely exemplary values. The x-axis of the plot 1090 is a spatial axis, which can be, for example, a distance beneath the skin S. The y-axis of the plot 1090 can have any relative value, such as, for example, current in Amperes.

As shown in FIG. 14, the highest amounts of current distribution within the body B is the area between the skin S (axis=0) and the target location T. Thus, the amount of current distribution within the body B can be adjusted or tuned by the positioning of the electrodes of an electrical stimulation system and/or the depth of a stimulation portion of an electronic implant.

FIGS. 12 and 14, combined, provide a 3D illustration of the net current distribution in the body B. As described above, the positioning of the electrodes 875, 876, 975 and 976 of the electrical stimulation systems 870 and 970 on the skin S and/or the positioning of the electronic implants 810 and 910 within the body can facilitate the adjustment of the magnitude of current reaching the target location T such that a desired stimulation at the target location T can be attained. For example, in some embodiments, the length of the electronic implant can be shortened such that the first electrode is positioned on the skin above the terminal portion of the electronic implant and the second electrode is positioned on the skin above the stimulation portion of the electronic implant. In this manner, the distance the first portion and the second portion of the electrical signal has to travel to the target location T is minimized such that attenuation of the electrical signal is minimized. As a result, a greater magnitude of current reaches the target location T.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the electrical signal is shown and described above as being an electrical current, in some embodiments, the electrical signal can be any stimulation signal to facilitate the stimulation of the target location T. For example, in some embodiments, the electrical signal can be an ultrasonic stimulation wave. In other embodiments, the electrical signal can be a radio frequency signal, an optical signal, a sonic signal or the like.

Although the electrodes 875, 876, 975 and 976 are shown and described above as being coupled to the skin S to provide transcutaneous electrical stimulation to a target location T within the body B, in some embodiments, at least an electrode 875, 876, 975 and 976 can be disposed within the body B to provide subcutaneous electrical stimulation to a target location T within the body B.

In some embodiments, the electrical stimulation system 870 and 970 can be configured to tune the timing of the stimulation to the target location T. For example, in some embodiments, the electrodes 875, 876, 975 and 976 can be positioned on the skin S relative to the electronic implant 810 and 910 and/or target location T such that the first portion $I_1$ and $I_3$ of the electrical signal and the second portion $I_2$ and $I_4$ of the electrical signal stimulates the target location T at the same time. In other embodiments, the electrodes 875, 876, 975 and 976 can be positioned to produce a phase difference between the first portion $I_1$ and $I_3$ of the electrical signal and the second portion $I_2$ and $I_4$ of the electrical signal such that the first portion $I_1$ and $I_3$ of the electrical signal and the second portion $I_2$ and $I_4$ of the electrical signal stimulate the target location T at different times. In some such embodiments, the timing of the stimulation can be adjusted based on the position of the electrodes 875, 876, 975 and 976 on the skin relative to the electronic implant 810 and 910 and/or target location T.

In some embodiments, the proximal end portion 102 of the insertion tool 100 can include an electronic device configured to convey information back to a user. Such information can be, for example, information relating to the location of the insertion tool 100 within the body B. In other embodiments, the proximal end portion 102 of the insertion tool 100 can be configured to electrically stimulate a target location within the body B.

In some embodiments, the proximal end portion 102 of the insertion tool 100 is configured to locate a target location within the body B. For example, in some embodiments, the proximal end portion 102 of the insertion tool 100 can include a target probe having an exposed electrode configured to stimulate a muscle, a nerve or the like and/or receive an electronic signal from a muscle, nerve or the like to locate the target location.

In some embodiments, the insertion tool 100 can include a plurality of graduated markings configured to indicate a position of the proximal end portion 102 of the insertion tool 100 within the body B. In some embodiments, the insertion tool 100 can be configured to have an adjustable length.

Although various embodiments have been described as having particular features and/or combinations of components, other embodiments are possible having a combination of any features and/or components from any of embodiments where appropriate. For example, in some embodiments, the insertion tool 100 can include a handle coupled to a distal end portion (not shown in FIG. 1) of the insertion tool 100 to facilitate the maneuvering of the insertion tool 100 within the body B. The handle could be, for example, the handle 650 of the implant delivery tool 600 illustrated in FIG. 8.

What is claimed is:

1. An apparatus, comprising:
   an insertion member configured to be coupled to at least a portion of an electronic implant for delivery of the portion of the electronic implant into a body, the insertion member including a distal end portion configured to be inserted within the body; and
   a guide member including a distal end portion configured to engage an outer surface of the body, the distal end portion of the guide member being displaced from the distal end portion of the insertion member by a predetermined distance, the guide member coupled to the insertion member such that movement of the distal end portion of the guide member in a first direction along the outer surface of the body results in movement of the distal end portion of the insertion member within the body such that the predetermined distance is substantially maintained, the distal end portion of the guide member including an electronic device configured to at least one of convey information to a user or electrically stimulate at least a target location within the body.

2. The apparatus of claim 1, wherein the distal end portion of the insertion member includes an electrode configured to stimulate at least a portion of the body.

3. The apparatus of claim 1, wherein the distal end portion of the insertion member is configured to receive an electronic signal from the body.

4. The apparatus of claim 1, further comprising:
   the electronic implant configured to stimulate the target location within the body.

5. The apparatus of claim 1, wherein the distal end of the guide member is laterally offset from the distal end portion of the insertion member during delivery of the portion of the electronic implant into the body.

6. The apparatus of claim 1, wherein the insertion member is configured to percutaneously deliver the portion of the electronic implant into the body.

7. The apparatus of claim 1, further comprising:
   the electronic implant, the electronic implant being a passive electrical conductor.

8. The apparatus of claim 1, wherein at least a portion of the insertion member is arcuate.

9. The apparatus of claim 1, wherein the insertion member defines a lumen configured to receive the portion of the electronic implant.

10. The apparatus of claim 1, wherein the insertion member includes a plurality of graduated markings configured to indicate a position of a distal end portion of the insertion member within the body.

11. The apparatus of claim 1, further comprising:
    a handle configured adjust an angle of orientation between the guide member and the insertion member.

12. The apparatus of claim 1, further comprising:
    a handle configured to adjust the distance between the distal end portion of the guide member and the distal end portion of the insertion member.

* * * * *